United States Patent
Yu et al.

(10) Patent No.: US 7,244,518 B2
(45) Date of Patent: Jul. 17, 2007

(54) ANTHRACENE COMPOUNDS AND ORGANIC ELECTROLUMINESCENT DEVICE EMPLOYING THE SAME

(75) Inventors: Chen-Ping Yu, Longtan Township, Taoyuan County (TW); Wen-Kuen Chen, Jhubei (TW)

(73) Assignee: AU Optronics Corp., Hsinchu (TW)

( * ) Notice: Subject to any disclaimer, the term of this patent is extended or adjusted under 35 U.S.C. 154(b) by 141 days.

(21) Appl. No.: 11/030,433

(22) Filed: Jan. 6, 2005

(65) Prior Publication Data

US 2006/0008674 A1 Jan. 12, 2006

(30) Foreign Application Priority Data

Jul. 6, 2004 (TW) .............................. 93120206 A (51) Int. Cl.
*H01L 51/50* (2006.01)
*C09K 11/06* (2006.01)
*C07F 7/08* (2006.01)

(52) U.S. Cl. ...................... 428/690; 428/917; 428/448; 313/504; 313/506; 252/301.16; 556/432; 257/103

(58) Field of Classification Search ................ 428/690, 428/917, 448; 313/504, 506; 252/301.16; 556/432; 257/103, E51
See application file for complete search history.

(56) References Cited

U.S. PATENT DOCUMENTS

| 6,310,231 | B1 | 10/2001 | Igarashi et al. ............. 556/489 |
| 6,465,115 | B2 | 10/2002 | Shi et al. .................... 428/690 |
| 6,534,199 | B1 | 3/2003 | Hosokawa et al. ......... 428/690 |
| 6,603,150 | B2 * | 8/2003 | Liao et al. .................... 257/98 |
| 2002/0055013 | A1 | 5/2002 | Kim et al. .................. 428/690 |

FOREIGN PATENT DOCUMENTS

JP 2002-121547 * 4/2002

OTHER PUBLICATIONS

Molecular Crystals and Liquid Crystals Science and Technology, Section A: Molecular Crystals and Liquid Crystals, 377, p. 19-23, (2002).*
Kim, Yun-Hi et al., Advanced Functional Materials, (2005), 15, p. 1799-1805.*
China Office Action dated Jan. 20, 2006.

* cited by examiner

*Primary Examiner*—Dawn L. Garrett
(74) *Attorney, Agent, or Firm*—Thomas, Kayden, Horstemeyer & Risley (57) ABSTRACT

Anthracene compounds and organic electroluminescent devices employing the same. Anthracene compounds can serve as host materials for an blue organic electroluminescent device. Furthermore, the anthracene compounds can also serve as hole transport layer materials or electron transport layer materials for organic electroluminescent devices, by way of the silyl phenyl group thereof.

10 Claims, 1 Drawing Sheet

FIG. 1

ANTHRACENE COMPOUNDS AND ORGANIC ELECTROLUMINESCENT DEVICE EMPLOYING THE SAME

BACKGROUND

The invention relates to an anthracene compound and, more particularly, to an anthracene compound with two silyl-phenyl groups, serving as electroluminescent material for an organic electroluminescent device.

Recently, with the development and wide application of electronic products, such as mobile phones, PDA, and notebook computers, there has been increasing demand for flat display elements which consume less electric power and occupy less space. Organic electroluminescent devices are self-emitting, and highly luminous, with wider viewing angle, faster response speed, and simpler fabrication, making them the industry display of choice.

A typical organic electroluminescent device is known as a sandwich structured element and comprises an anode layer and a cathode layer, separated by organic electroluminescent layers. Electrons propelled from the cathode layer and holes propelled from the anode layer, create an electric field inducing a potential difference, such that the electrons and holes move and centralize in the organic electroluminescent layers, resulting in luminescence through recombination thereof.

Anthracene compounds have been widely used in materials of organic electroluminescent layers. U.S. Pat. No. 6,465,115 discloses an anthracene derivative used as hole transport layer material having the structure:

wherein $R^1$, $R^2$, $R^3$, and $R^4$ are each independently $C_{1-24}$ alkyl group, $C_{5-20}$ aryl group, or $C_{5-20}$ heteroaryl group.

U.S. Pat. No. 6,534,199 discloses an anthracene derivative used as a light-emitting layer material having the structure:

U.S. Pat. No. 6,310,231 discloses an aryl silane having the structure:

However, these and other conventionally used compounds present considerable complexity of fabrication and low electroluminescent luminescent efficiency used in organic electroluminescent devices. Further improvements in organic electroluminescent compound are required in a variety of flat panel display applications.

SUMMARY

Embodiments of the invention provide anthracene compounds having the structure showing in formula (I):

Accordingly, $R^5$ and $R^6$ are each independently hydrogen, substituted or unsubstituted $C_{6-20}$ aryl group, substituted or unsubstituted heteroaryl group having 2 to 5 carbon atoms, or substituted or unsubstituted $C_{1-12}$ alkyl group, and $R^7$ are each independently substituted or unsubstituted $C_{6-20}$ aryl group, or substituted or unsubstituted $C_{1-12}$ alkyl group, wherein the substituent is $C_{1-10}$ alkyl, $C_{1-10}$ alkoxy, phenyl, or halogen. Furthermore, at least one hydrogen atom bonded to the carbon atom of the anthracene compound according to formula (I) is substituted optionally by $C_{1-10}$ alkyl group, $C_{1-10}$ alkoxy group, phenyl group, or halogen atom.

Further provided is an organic electroluminescent device comprising an anode, a cathode, and organic electroluminescent layers therebetween, wherein the electroluminescent layers comprises the anthracene compound according to formula (I).

A detailed description is given in the following with reference to the accompanying drawing.

BRIEF DESCRIPTION OF THE DRAWINGS

The invention can be more fully understood by reading the subsequent detailed description in conjunction with the examples and references made to the accompanying drawing, wherein.

DETAILED DESCRIPTION

The recognition properties of embodiments of anthracene compounds depend significantly on silyl-phenyl substituents at the 9- and 10-positions of the anthracene group. Particularly, the anthracene compounds can have the structure showing in formula (I):

Accordingly, $R^5$ and $R^6$ are each independently hydrogen, substituted or unsubstituted $C_{6-20}$ aryl group, substituted or unsubstituted heteroaryl group having 2 to 5 carbon atoms, or substituted or unsubstituted $C_{1-12}$ alkyl group. Preferably, $R^5$ and $R^6$ are each independently hydrogen, substituted or unsubstituted $C_{6-10}$ aryl group, substituted or unsubstituted heteroaryl group having 4 to 5 carbon atoms, or substituted or unsubstituted $C_{1-4}$ alkyl group.

$R^7$ are each independently substituted or unsubstituted $C_{6-20}$ aryl group, or substituted or unsubstituted $C_{1-12}$ alkyl group. Preferably, $R^7$ are each independently substituted or unsubstituted $C_{6-10}$ aryl group, or substituted or unsubstituted $C_{1-3}$ alkyl group.

For $R^5$, $R^6$, and $R^7$, the substituted or unsubstituted $C_{6-20}$ aryl group includes, but is not limited to, phenyl, 2-methyl phenyl, 3-methyl phenyl, 4-methyl phenyl, 4-ethyl phenyl, biphenyl, 4-methyl biphenyl, 4-ethyl biphenyl, 4-cyclohexyl biphenyl, terphenyl, 3,5-dichlorophenyl, naphthyl, 5-methyl naphthyl, anthryl, or pyrenyl.

For $R^5$, $R^6$, and $R^7$, the substituted or unsubstituted $C_{1-12}$ alkyl group includes, but is not limited to, methyl, ethyl, propyl, butyl, sec-butyl, tert-butyl, pentyl, hexyl, heptyl, octyl, 2-phenylisopropy, trichoromethyl, or trifluoromethyl.

Furthermore, at least one hydrogen atom bonded to the carbon atom of the anthracene compound according to formula (I) can be substituted optionally by $C_{1-10}$ alkyl group, $C_{1-10}$ alkoxy group, phenyl group, or halogen atom.

Moreover, the anthracene compounds having the structure showing in formula (I) can be

-continued

-continued

, or min, 2.5 g (12 mmol) anthracene with 30 ml THF added dropwise slowly into the round-bottom flask at −78° C. After reacting at room temperature for 24 hours, the resulting mixture was subjected to extraction with a mixed solvent (ethyl acetate:$H_2O$), dried over anhydrous $MgSO_4$, filtered, and condensed, giving intermediate (1).

4.7 g (29 mmol) of Potassium iodide, 6.8 g (58 mmol) of sodium hypophosphite monohydrate, 50 ml of acetic acid and intermediate (1) were added into a reaction bottle and heated to reflux for 2 hours. After cooling, white precipitation in the bottle was collected and purified by column chromatography, giving 4.5 g of intermediate (2). The reaction according to preparation of the above is shown below.

The following examples are intended to illustrate the invention more fully without limiting their scope, since numerous modifications and variations will be apparent to those skilled in this art.

FIRST EXAMPLE

Anthracene Compound (I):

In a nitrogen atmosphere, 5.7 g (24 mmol) of 1,3-dibromo benzene, and 100 ml of tetrahydrofuran (THF) were added to a round-bottom flask. Next, 9.6 ml (24 mmol, 2.5M) of n-butyl lithium was added dropwise slowly into the round-bottom flask at −78° C. After mixing and reacting for 30

6 g (12.3 mmol) of intermediate (2) was dissolved in 150 ml of anhydrous THF. Next, 11.3 ml (27 mmol, 2.4M) of n-butyl lithium was added dropwise slowly into the solution. After mixing and reacting for 30 min, 8 g (27.1 mmol) of triphenylsilyl chloride (dissolved with 20 ml THF) was added dropwise slowly into the above solution at −78° C. After reacting at room temperature for 16 hours, the resulting mixture was filtered, washed with a mixture solvent (ethanol:hexane=1:1), and condensed, giving a crude product as a white solid which was purified by sublimation to obtain 4.0 g of anthracene compound (I). The reaction according to preparation of the above is shown below.

intermediate (2)

anthracene compound (I)

The analysis data:
1H NMR (400 MHz, CDCl3): δ 7.3~7.5(m, 23H), 7.5~7.7 (m, 15H), 7.7~7.84(m, 8H). FAB-MS: m/e=847 (M+)

SECOND EXAMPLE

Anthracene Compound (II):

Example 2 was performed as Example 1 except for substitution of 1,4-dibromo benzene for 1,3-dibromo benzene 0.03 ml. After purification, anthracene compound (II) was obtained. The reaction according to Example 2 is shown below.

Figure 1:
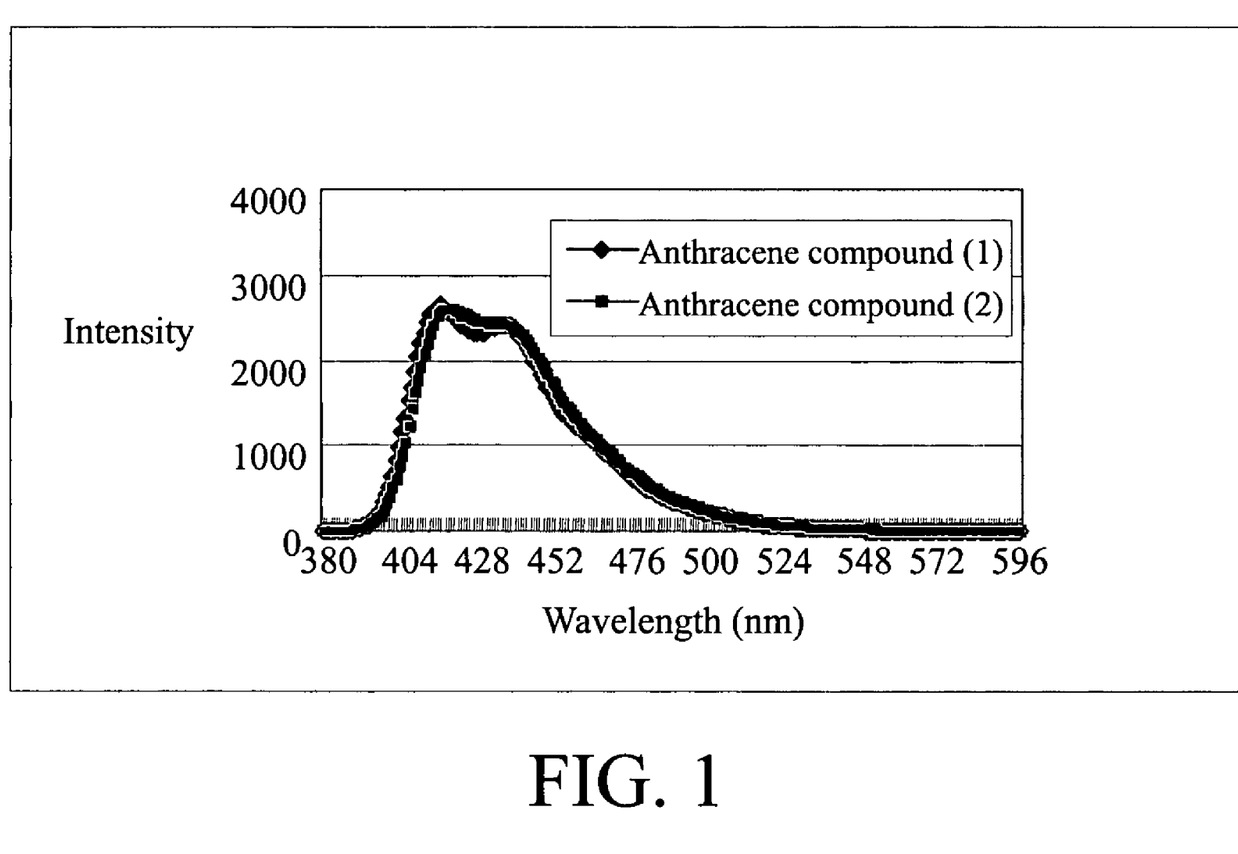
FIG. 1 is a photoluminescence spectrum plotting wavelengths against intensity of embodiments of anthracene compounds (1) and (2).

The photoluminescence spectrum as shown in FIG. 1 illustrates that both anthracene compounds (1) and (2) emit blue light with maximum emission wavelength of 420 nm.

Further provided is an organic electroluminescent device comprising a glass substrate with indium tin oxide (ITO)

film, a hole injection layer, a hole transport layer, a light-emitting layer, an electron transport layer, a lithium fluoride layer, and an aluminum electrode, bonded in that order. The hole injection layer, hole transport layer, light-emitting layer, and electron transport layer act as electroluminescent layers, at least one of which comprises anthracene compounds, embodiments of which are provided by the formula (I):

such as anthracene compound (I) (disclosed in Example 1) or anthracene compound (II) (disclosed in Example 2).

DEVIC EXAMPLE 1

A glass substrate with indium tin oxide (ITO) film of 750 nm was provided and then washed by cleaning agent, acetone, and ethanol with ultrasonic agitation. After drying with nitrogen flow, the ITO film was subjected to uv/ozone treatment. Next, A hole injection layer, hole transport layer, light-emitting layer, electron transport layer, lithium fluoride layer, and aluminum electrode were subsequently formed on the ITO film at 10-4 Pa, obtaining the organic electroluminescent device (1). For purposes of clarity, the materials and layers formed therefrom are described as below.

The hole injection layer, with a thickness of 60 nm, consisted of 2T-NATA (4,4',4''-tri(N-(2-naphthyl)-N-aniline)-triphenyl amine). The hole transport mixed layer 340, with a thickness of 30 nm, consisted of NPB (N,N'-di-1-naphthyl-N,N'-diphenyl-1,1'-biphenyl-1,1'-biphenyl-4,4'-diamine). The light-emitting layer 360 with a thickness of 30 nm, consisted of TBPe (2,5,8,11-Tetra-tert-butyl-perylene) as dopant, and anthracene compound (I) (disclosed in Example 1) as light-emitting material, wherein the weight ratio between anthracene compound (I) and dopant was 100:2.5. The electron transport layer, with a thickness of 30 nm, consisted of $Alq_3$ (tris(8-hydroxyquinoline)aluminum). The lithium fluoride layer has a thickness of 10 Å and the aluminum electrode a thickness of 100 nm.

The emissive structure of the organic electroluminescent device (1) can be represented as below:

ITO 750 nm/2T-NATA 60 nm/NPB 300 Å/anthracene compound (I):TBPe 100:2.5 30 nm/$Alq_3$ 30 nm/LiF 10 Å/Al 100 nm The measured results of optical properties for the organic electroluminescent device (1), as described in device example 1, are shown in Table 1.

TABLE 1

Optical Properties for Device Example 1

| Current Density ($mA/cm^2$) | Brightness ($cd/m^2$) | CIE chromaticity coordinates (X axis) | CIE chromaticity coordinates (Y axis) | Efficiency (cd/A) |
| --- | --- | --- | --- | --- |
| 24 | 770 | 0.15 | 0.18 | 3.2 |

The anthracene compounds according to formula (I) exhibit photoluminescent and electroluminescent properties. In some embodiments of the invention, organic electroluminescent devices empolying the anthracene compounds, acting as host materials, emit blue light with high luminescent efficiency under bias voltage. Furthermore, the anthracene compounds according to formula (I) can also serve as hole transport layer materials or electron transport layer materials for organic electroluminescent devices, due to the silyl phenyl group thereof.

While the invention has been described by way of example and in terms of preferred embodiment, it is to be understood that the invention is not limited thereto. It is therefore intended that the following claims be interpreted as covering all such alteration and modifications as fall within the true spirit and scope of the invention.

What is claimed is:

1. An anthracene compound having a formula (I), of:

wherein

$R^5$ and $R^6$ are each independently hydrogen, substituted or unsubstituted $C_{6-20}$ aryl group, substituted or unsubstituted heteroaryl group having 2 to 5 carbon atoms, or substituted or unsubstituted $C_{1-12}$ alkyl group; and

$R^7$ are each independently substituted or unsubstituted $C_{1-12}$ aryl group, wherein the substituent is $C_{1-10}$ alkyl, $C_{1-10}$ alkoxy, phenyl, or halogen.

2. The anthracene compound as claimed in claim 1, wherein at least one of $R^7$ is methyl group.

3. The anthracene compound as claimed in claim 1, wherein the anthracence compound is

-continued wherein at least one hydrogen atom bonded to a carbon atom of the anthracene compound is substituted optionally by $C_{1-10}$ alkyl group, $C_{1-10}$ alkoxy group, phenyl group, or halogen atom.

4. An emissive structure for an organic electroluminescent device, comprising the anthracene compound as claimed in claim 1.

5. The emissive structure as claimed in claim 4, wherein the anthracene compound is host material.

6. An organic electroluminescent device, comprising:
a substrate;
an anode formed on the substrate;
an organic electroluminescent layer formed on the anode; and
a cathode formed on the organic electroluminescent layer, wherein,
the organic electroluminescent layers comprise an anthracene compound having a formula (I), of:

wherein
$R^5$ and $R^6$ are each independently hydrogen, substituted or unsubstituted $C_{6-20}$ aryl group, substituted or unsubstituted heteroaryl group having 2 to 5 carbon atoms, or substituted or unsubstituted $C_{1-12}$ alkyl group; and
$R^7$ are each independently substituted or unsubstituted $C_{1-12}$ aryl group, wherein the substituent is $C_{1-10}$, $C_{1-10}$ alkoxy, phenyl, or halogen.

7. The device as claimed in claim 6, wherein at least one of $R^7$ is phenyl group.

8. The anthracene compound as claimed in claim 1, wherein the anthracene compound is , or wherein at least one hydrogen atom bonded to a carbon atom of the anthracene compound is substituted optionally by $C_{1-10}$ alkyl group, $C_{1-10}$ alkoxy group, phenyl group, or halogen atom.

9. The device as claimed in claim 6, wherein the organic electroluminescent layer comprises a light-emitting layer with the anthracene compound according to formula (I).

10. The device as claimed in claim 9, wherein the light-emitting layer is a blue light-emitting layer comprising the anthracene compound as host material.

* * * * *